United States Patent [19]

Marchal et al.

[11] Patent Number: 5,616,479
[45] Date of Patent: Apr. 1, 1997

[54] METHOD OF PRODUCTION OF SOPHOROSIDES BY FERMENTATION WITH FED BATCH SUPPLY OF FATTY ACID ESTERS OR OILS

[75] Inventors: Remy Marchal, Chatou; Jeannine Lemal; Caroline Sulzer, both of Rueil Malmaison, all of France

[73] Assignee: Institut Francais du Petrole, Rueil Malmaison, France

[21] Appl. No.: 920,575

[22] PCT Filed: Dec. 17, 1991

[86] PCT No.: PCT/FR91/01027

§ 371 Date: Aug. 19, 1992

§ 102(e) Date: Aug. 19, 1992

[87] PCT Pub. No.: WO92/11381

PCT Pub. Date: Jul. 9, 1992

[30] Foreign Application Priority Data

Dec. 20, 1990 [FR] France ................... 90 16211

[51] Int. Cl.$^6$ .............. C12P 19/12; C12P 7/42; C12P 1/02
[52] U.S. Cl. .......................... 435/100; 435/146; 435/171
[58] Field of Search ......................... 435/100, 146, 435/171

[56] References Cited

U.S. PATENT DOCUMENTS 3,205,150  9/1965  Spencer ....................... 435/146
4,297,340 10/1981 Abe ............................ 424/70

OTHER PUBLICATIONS

Hans–Joachim Asmer et al., "Microbial Production, Structure Elucidation, and Bioconversion of Sophorose Lipids," *Journal of the American Oil Chemists' Society*, vol. 65, No. 9, Sep. 1988, pp. 1460–1466.

Inoue, S., "Biosurfactants in Cosmetic Applications", *Proc. World Conference on Biotech for the Fats and Oils Industry*, pp. 206–209, 1988.

*Primary Examiner*—Michael G. Wityshyn
*Assistant Examiner*—L. Blaine Lankford
*Attorney, Agent, or Firm*—Millen, White, Zelano, & Branigan, P.C.

[57] ABSTRACT

The invention relates to a fed batch production process for a composition of sophorosides, in which culturing takes place of at least one *Candida bombicola* or *Candida apicola* strain and the cultured strain is exposed in a reaction zone to an excess sugar supply and a continuous supply of at least one appropriate substrate at a supply rate to the reaction zone between 0.01 and 4 grams per hour and per liter of initial reaction volume and for a supply time such that the residual concentration of the substrate in the reaction zone is maintained at a value at the most equal to 18 grams per liter of initial reaction volume for the supply time and the composition of sophorosides produced is recovered.

23 Claims, No Drawings

METHOD OF PRODUCTION OF SOPHOROSIDES BY FERMENTATION WITH FED BATCH SUPPLY OF FATTY ACID ESTERS OR OILS

BACKGROUND OF THE INVENTION

The invention relates to a process for the production, with a continuous supply of the substrate (fed batch) of a sophoroside composition by fermentation. Sophorosides are e.g. used in cosmetology, in dandruff treatment for hair and as a bacteriostatic agent in deodorants, particularly in lactone form (EP-B-209783.

It is stated in U.S. Pat. Nos. 3,205,150 and 3,312,684 that a quantity of sophorosides was produced by a Fermentation process using a *Torulopsis bombicola* culture the strain presently classified as *Candida bombicola*.

Sophorosides are considered as being a mixture of the compounds represented by Formulas (1) and (2):

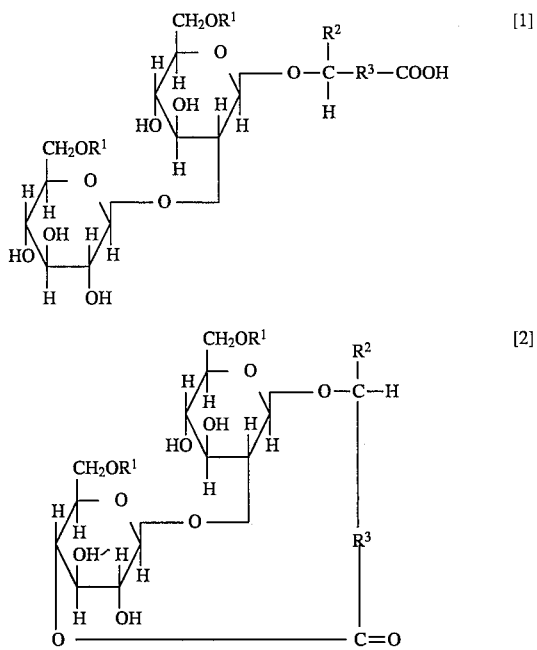

in which $R^1$ represents hydrogen or an acetyl group and $R^2$ hydrogen or an alkyl group having 1 to 9 carbon atoms, when $R^3$ is a saturated hydrocarbon radical with 7 to 16 carbon atoms, or $R^2$ represents hydrogen or a methyl group, when $R^3$ is an unsaturated hydrocarbon radical with 13 to 17 carbon atoms.

These compounds can be used as cleaning agents and emulsifiers and have excellent hygroscopic and hydrophilic properties due to the sophorose group and hydrophobic properties as a result of the Fatty acid.

However, sophorosides are a group of numerous homo logs and the formation ratio of these homologs varies as a function of their substrate, e.g. a hydrocarbon source, as well as the fermentation conditions (FR-A-2399438). Consequently, the properties and functions of these compounds vary with the ratios of the homologs, bearing in mind that use is generally made of a group of said homologs and it has hitherto been difficult to be able to produce a product having a given ratio using a fermentation process.

The prior art is illustrated by the document "Journal of the Americal Oil Chemists Society, vol.65, No. 9, September 1988, Champaign, Ill., USA, pages 1460–1466: H. J. ASMER et al— "Microbial production, structure elucidation and bioconversion of sophorose lipids."

Sophorosides are generally prepared in the presence of a substrate, such as is e.g. described in U.S. Pat. No. 3,205, 150. for example, said substrate can be in the form of hydrocarbons, saturated or unsaturated fatty acids, acid esters including glycerides, vegetable oils such as soybean oil, etc. Supply generally takes place discontinuously at time intervals of approximately 12 to 24 hours and with a quantity of approximately 2% by weight, based on the initial reaction volume, for each addition.

It is stated that the presence of a higher substrate quantity (3 to 4% approximately) leads to a reduction in the yield of sophorosides produced. Moreover, 24 to 48 hours following the final substrate addition, no supplementary conversion is observed.

This batch production process is also described in U.S. Pat. No. 4,297,340, where a substrate quantity (150 g) is added every 24 hours for 6 days, the total culture production time being 7 days.

These discontinuous supply processes make it possible to reach final crude sophoroside production levels not exceeding 23%, so that yields are limited. The reason for this limitation is the lipolytic capacity of the microorganism, which transforms the residual esters or oils of the fermentation medium into fatty acids. These fatty acids are not inhibitors to microorganism growth, but they are liable to significantly affect the sophoroside production speed, when already present in the medium.

SUMMARY OF THE INVENTION

The object of the invention is to obviate the disadvantages of the prior art. A process for the preparation of sophorosides has been discovered, which in particular makes it possible to improve the productivity of the cultured strain, the yield of sophorosides produced and therefore the production of the sought sophorosides.

In a more detailed manner, the invention relates to a process for the fed batch production of a composition of sophorosides, in which culturing takes place of at least one *Candida bombicola* or *Candida apicola* strain in a culture medium including a nitrogen source under appropriate conditions for producing said strain and the cultured strain is exposed in a reaction zone to a preferably excess sugar supply and a continuous supply of at least one appropriate substrate under adequate aeration, temperature and pH conditions, characterized in that the following sequence is performed at least once:

a. the strain is supplied with said substrate at a supply flow rate in the reaction zone between 0.01 and 4 grams per hour and per liter of initial reaction volume and for a supply time such that the residual concentration of said substrate in the reaction zone is kept at a value at the most equal to 18 grams per liter of initial reaction volume for said supply time and b. the composition of sophorosides produced is recovered. In a preferred manner, the continuous substrate supply can take place according to a time-decreasing profile.

According to a feature of the process, the sophoroside composition recovery stage comprises the stoppage of the substrate supply or the aeration of the reaction zone, the recovery, after settling, of the lower sophoroside phase containing water and at least one washing with water of the sophorosides at a temperature generally between 10° and 90° C. for e.g. 10 to 60 min.

The strain used is advantageously *Candid bombicola* CBS 6009. The productivity observed is then excellent and the yield of sophorosides produced is well above that of the prior art.

The process can be performed according to two embodiments. In the first embodiment, the substrate is supplied by regulating the supply rate to the reaction zone under the aforementioned operating conditions, the substrate supply being stopped when the total injected substrate quantity reaches approximately at the most 280 g·l$^{-1}$ of initial reaction volume and the sophoroside composition is recovered in the manner indicated hereinbefore. According to a second, more advantageous embodiment, the substrate is supplied by regulating the supply rate in the reaction zone under conditions such that the residual substrate concentration is close to a preferably fixed value generally between 0.1 and 18 and preferably between 0.5 and 3 g·l$^{-1}$. As soon as the $O_2$ concentration in the dissolved reaction zone advantageously approaches 0, the substrate supply and the stirring of the fermenter are stopped, the solution is allowed to settle, the sophoroside phase is recovered and washed at least once at a temperature between 10° and 90° C. and substrate is again supplied to the reaction zone freed from said sophoroside phase. It is thus possible to recommence this supply, settling and recovery sequence until the microorganism biosynthesis capacity is exhausted.

According to another feature of the process and the continuous supply, the reaction zone can initially optionally contain a sugar in excess and a substrate concentration of 0.5 to 40 g·l$^{-1}$ of initial reaction volume and advantageously 1 to 25 g·l$^{-1}$ and said strain is continuously supplied with substrate after a period of e.g. at the most 48 hours, i.e. when the initial substrate concentration is generally between 0.1 and 15 g·l$^{-1}$ per liter of initial reaction medium and preferably between 0.1 and 5 g·l$^{-1}$.

According to another advantageous feature of the process making it possible to obtain good results, the continuous substrate supply rate in the reaction zone can be between 1.0 and 3.0 g·h$^{-1}$·l$^{-1}$ of initial reaction volume and is preferably between 2.0 and 2.5 g·h$^{-1}$·l$^{-1}$.

This substrate generally incorporates at least one animal oil, at least one vegetable oil and/or at least one ester of said oil, said oils and said esters incorporating an aliphatic, straight chain in saturated or unsaturated form with 10 to 24 carbon atoms. Among the preferred oils and esters reference is made to the oil and methyl or ethyl esters of colza oil, sunflower seed oil, palm oil or soybean oil. Excellent results are obtained with said esters.

The culture medium can incorporate a mineral nitrogen source (in the form of ammonium ions) and/or organic nitrogen, e.g. in the form of amino acids such as in particular yeast extract, soybean peptone, casein hydrolyzates, maize/corn maceration liqueur, wheat gluten hydrolyzates and meat extracts. The addition of mineral elements such as e.g. potassium, sodium, magnesium and oligoelements such as iron, manganese, molybdenum in the form of their salts (sulphates, phosphates, chlorides) can also make it possible to further improve growth. The culture medium can incorporate at least one sugar such as glucose or saccharose.

The culture conditions are generally temperature 18° to 35° C. and pH 3 to 8. A good activity level has been obtained at a temperature between 20° and 30° C. in a pH range of 3 to 5 and excellent activity results are observed at a temperature between 22° and 28° C. and a pH between 3.5 and 4. Fermentation takes place under initial asepsis and aerobiosis conditions.

According to another feature of the process, it is possible to introduce the strain contained in the culture medium into the reaction zone in order to expose it to the substrate and sugar supply, but according to another feature of the process the strain can be removed from the culture medium by known procedures and introduced into the reaction zone, where it is exposed to the substrate and sugar supply.

The sophoroside production process is generally performed under the following conditions: temperature 18° to 35° C., pH 2.5 to 8 and advantageously 3 to 4, aeration flow rate 0.2 to 2 v.v.m. under a pressure of 1 to 5 and preferably 1 to 2 bar (1 bar=0.1 MPa).

Throughout the production time, the pH is checked and regulated to a desired value within the range described hereinbefore by e.g. adding potash or soda solution.

The quantity of cells used compared with the initial reaction volume is generally 1 to 100 g of dry weight per liter and preferably 10 to 30 g of dry weight per liter.

The invention will be better understood from the following non-limitative, illustrative examples:

EXAMPLE 1

This example describes a fermentation performed according to the invention. The strain *Candida bombicola* CBS 6009 is used for seeding a medium which, independently of the glucose, is deprived of substrate, which is continuously added following seeding. It is colza ethyl ester. The following culture medium is used:

| | |
|---|---|
| glucose | 100 g · l$^{-1}$ |
| $(NH_4)_2SO_4$ | 4 g · l$^{-1}$ |
| $KH_2PO_4$ | 1 g · l$^{-1}$ |
| $MgSO_4, 7H_2O$ | 0.5 g · l$^{-1}$ |
| dried corn maceration liqueur | 5.0 g · l$^{-1}$ |

Glucose and $MgSO_4, 7H_2O$ are sterilized in a 4 liter capacity laboratory fermenter dissolved in 1620 ml of water, whereas the $KH_2PO_4$, $(NH_4)_2SO_4$ and corn liqueur are separately sterilized in an Erlenmeyer flask dissolved in 180 ml of water. The sterilization of the two solutions takes place in the autoclave at a temperature of 120° C. and for 30 minutes and the culture medium is reconstituted after cooling the two solutions. It is seeded by 200 ml of a preculture prepared in an Erlenmeyer flask with 200 ml of the same medium as the fermentation medium, but to which has been added 1 ml of colza ethyl ester. This flask is seeded by approximately 1 g of a congelate of the *Candida bombicola* strain. It is incubated, accompanied by stirring, at 25° C. and after 24 hours supplies the fermenter preculture. The production fermentation takes place in the fermenter having a 4 liter capacity and on an initial reaction volume of 2 liters.

The medium is stirred by using a RAYNERI turbine, whose rotation speed is 1000 r.p.m. Aeration is fixed at 0.5 v.v.m. of air under atmospheric pressure. Following auto-acidification of the culture, the pH of the medium is kept at a constant value of 3.5 by a 4N soda solution, whose addition to the reactor is controlled by an electrovalve dependent on a pH-meter. The content of oxygen dissolved in the culture medium is continuously measured by means of a polarographic electrode connected to a recorder.

In order to prevent any glucose medium limitation, said sugar is added 5 times in solid form. On the three first occasions at times t=24 h, t=48 h, and t=72 h, each corresponding to 45 g of glucose per liter of initial medium, whereas the two latter at t=96 h and t=120 h each correspond to 32.5 g of glucose per liter. The colza ethyl ester supply is provided by means of a peristaltic pump, whose supply speed is fixed at 2 g·l$^{-1}$·h$^{-1}$ up to times t=96 h and then 1

$g \cdot l^{-1} \cdot h^{-1}$ up to time t=144 h. Sophoroside production is followed by taking samples and measurement takes place by the method of Göbbert et al (1984, Biotechnol. lett. 6, 225–230). This production, which starts with the growth of the microorganism, increases with colza ethyl ester addition. The residual concentration of the latter, measured by gas chromatography after hot extraction with heptane, is equal to 0.7 $g \cdot l^{-1}$.

After 144 h fermentation, stirring, aeration and ethyl ester supply are stopped and the crude sophorosides are allowed to settle for 1 hour. They are recovered and stirred with 1.5 l of distilled water at 45° C. They are again left to settle for 4 hours and a second washing takes place under the same conditions. Following the second washing, 565 g of crude sophorosides per liter of initial second are recovered. The productivity of the fermentation, calculated on the basis of the crude sophorosides and the duration of the test, is therefore 3.92 g of crude sophorosides per liter of initial medium and per hour. The water content of the crude sophorosides measured by the Karl-Fischer method is 45%. Taking account of the sugar arid ester quantities supplied and equal respectively to 300 and 240 $g \cdot l^{-1}$, the anhydrous sophoroside production yield based on the sum of the glucose plus ester is 59.5%. The production, productivity and yields were also measured after 96 hours of culture (immediately prior to the fourth glucose addition) for comparison with the discontinuous ester supply protocol (example 2). After 96 hours, the crude sophoroside production corresponds to 295 $g \cdot l^{-1}$ and therefore to a productivity of 3.07 $g \cdot l^{-1}$. The conversion yield of "glucose plus ethyl ester" in anhydrous sophorosides is then 38%.

EXAMPLE 2

(Comparison)

Example 1 is recommenced replacing the continuous colza ethyl ester supply by an addition every 12 hours of 20 $g \cdot l^{-1}$ of colza ethyl ester. The first addition took place immediately following the seeding of the fermenter. As in example 1, the crude sophoroside production kinetics in the fermentation medium is followed. It starts at the end of growth, but stops prematurely after 96 hours, at the same time as the 9th colza ethyl ester addition. On continuing ethyl ester additions, it would also be impossible to recover by settling the sophorosides, which remain intimately mixed with the residual ethyl ester. After 96 hours only 210 $g \cdot l^{-1}$ of crude sophorosides have been recovered. The productivity, based on the crude sophorosides and the 96 hour period, is equal to 2.18 $g \cdot l^{-1} \cdot h^{-1}$. The conversion yield of "glucose (235 $g \cdot l^{-1}$) plus colza ethyl ester (180 $g \cdot l^{-1}$)" in anhydrous sophorosides (moisture content 45%) is 27.8%. These performance figures are below those obtained for the same time in example 1.

EXAMPLE 3

Example 1 is repeated up to t=95, at which there is a substantially total exhaustion of the dissolved oxygen of the medium. During this first period, the residual colza ethyl ester concentration in the fermentation medium is 0.5 $g \cdot l^{-1}$. Stirring, aeration and ester supply are stopped for 15 minutes and the sophorosides which have settled are drawn off. Aeration, stirring and ester supply of the fermenter are recommenced and the test is continued in the following way: 45 $g \cdot l^{-1}$ of glucose are added at t=96 h and t=120 h and then 32.5 $g \cdot l^{-1}$ at t=144 h. At the 96th hour, there is a reduction in the ethyl ester supply rate from 2 to 1.6 $g \cdot l^{-1} \cdot h^{-1}$ and the supply is continued at this rate up to t=144 h. At this time, the ester supply rate is again reduced to 0.92 $g \cdot l^{-1} \cdot h^{-1}$ to t=168 h. This is followed by a second recovery of sophoroside by settling and the microorganism biosynthesis capacity has not been exhausted. The crude sophorosides recovered at t=95 h and t=168 h are combined and washed twice, as in example 1. This gives 705 $g \cdot l^{-1}$ of crude sophorosides after 168 h of culture. The fermentation productivity based on the duration of the test is 4.19 $g \cdot l^{-1} \cdot h^{-1}$ for a supplied sugar quantity of 357.5 $g \cdot l^{-1}$ and an ethyl ester quantity of 290 $g \cdot l^{-1}$. The anhydrous sophoroside yield is 59.8%, based on the two substrates.

EXAMPLE 4

Example 1 is repeated adding 24 $g \cdot l^{-1}$ of colza ethyl ester to the culture medium and the continuous ethyl ester addition is started 12 hours following seeding. The injection speed is fixed at 2 $g \cdot l^{-1} \cdot h^{-1}$ up to t=96 h and then 1 $g \cdot l^{-1} \cdot h^{-1}$ up to 144 h. After 144 hours, 550 g of crude sophorosides are recovered per liter of initial medium. The productivity relative to the crude sophorosides is 3.82 $g \cdot l^{-1} \cdot h^{-1}$ and the anhydrous sophoroside yield is 56%.

EXAMPLE 5

Example 1 is repeated replacing the colza ethyl ester by colza methyl ester. At the end of the test, 525 g of crude sophorosides are recovered, which corresponds to a productivity of 3.64 $g \cdot l^{-1} \cdot h^{-1}$ of crude sophorosides and a yield of 53.4% of anhydrous sophorosides, based on the sum "glucose plus ester".

EXAMPLE 6

Example 1 is repeated replacing the colza ethyl ester by sunflower seed methyl ester. At the end of the Lest 505 $g \cdot l^{-1}$ of crude sophorosides are recovered, which corresponds to a productivity of 3.50 $g \cdot l^{-1} \cdot h^{-1}$ and a yield of 51.4% of anhydrous sophorosides, based on the sum "glucose plus methyl ester".

EXAMPLE 7

Example 1 is repeated replacing the colza methyl ester by colza oil. The oil injection speed is fixed at 1.2 $g \cdot l^{-1} \cdot h^{-1}$ up to t=96 h and then 0.60 $g \cdot l^{-1} \cdot h^{-1}$. The first three glucose additions at t=24 h, t=48 h and t=72 h correspond in each case to 30 $g \cdot l^{-1}$, while the two last at t=96 h and t=120 h each correspond to 20 $g \cdot l^{-1}$ of initial medium. After e.g. 144 hours culture, there is a recovery of 380 g of crude sophorosides corresponding to a productivity of 2.64 $g \cdot l^{-1} \cdot h^{-1}$ of crude sophorosides and a 53% yield of anhydrous sophorosides (moisture content 45%).

We claim:

1. In a process for the fed batch production of a composition of sophorosides, comprising culturing a single strain of *Candida bombicola* or *Candida apicola* in a culture medium containing a nitrogen source and a substrate under aerated culturing conditions in a reaction zone, the improvement comprising:

(a) continuously feeding said substrate to the strain in the reaction zone at a flow rate of between 0.01 and 4 grams of substrate per hour and per liter of initial reaction volume, and maintaining the residual concentration of said substrate in the reaction zone at a concentration not exceeding 18 gram per liter of initial reaction volume while said substrate is being continuously fed to the reaction zone, (b) recovering the resultant composition of sophorosides, wherein said substrate is at least one of an animal oil, a vegetable oil, or an ester of said animal or vegetable oil, said animal or vegetable oil or said ester comprising an aliphatic, straight chain with 10 to 24 carbon atoms.

2. A process according to claim 1, wherein the strain is *Candida bombicola.*

3. A process according to claim 1, wherein the strain is *Candida apicola.*

4. A process according to claim 1, wherein the sophoroside composition recovery stage (b) comprises stopping the substrate supply or the aeration of the reaction zone; permitting the resultant culture medium to settle to form a lower sophoroside phase containing water; recovering said lower phase and washing the lower phase of sophorosides with water at a temperature between 10° and 90° C. for 10 to 60 minutes.

5. A process according to claim 1, wherein the substrate supply is stopped when the oxygen concentration in the reaction zone is substantially equal to 0.

6. A process according to claim 1, wherein the substrate supply is stopped when the total injected substrate quantity reaches at the most 280 $g \cdot l^{-1}$ of initial reaction volume.

7. A process according to claim 1, wherein sophoroside production takes place at a temperature of 18° to 35° C., at a pH of 2.5 to 8, in the presence of a sugar excess and in which the reaction zone is aerated at a rate of 0.2 to 2 v.v.m. under a pressure of 1 to 5 bar.

8. A process according to claim 1, wherein the strain is obtained from an ex-situ prepared culture.

9. A process according to claim 1, wherein the cell concentration is 1 g to 100 g of dry weight per liter of reaction volume.

10. A process according to claim 1, wherein the residual substrate concentration is maintained at between 0.5 and 3 $g \cdot l^{-1}$.

11. A process according to claim 1, wherein said continuous feeding is initiated directly after the reaction zone is seeded with said strain.

12. A process according to claim 1, wherein the culture medium comprises sugar.

13. A process according to claim 12, wherein the sugar is added to the culture medium in an excess concentration.

14. A process according to claim 1, wherein the substrate flow rate into the reaction zone is between 1.0 and 3.0 $g \cdot l^{-1} \cdot h^{-1}$ of initial reaction volume.

15. A process according to claim 14, wherein the flow rate is between 2 and 2.5 $g \cdot h^{-1} \cdot l^{-1}$.

16. A process according to claim 1, wherein the strain contained in the culture medium is cultured with the substrate and with added sugar.

17. A process according to claim 16, wherein the sugar is added to the culture medium in an excess concentration.

18. A process according to claim 16, wherein said flow rate of continuous feeding of the substrate is decreased at least once during said culturing and the culturing is continued at said decreased flow rate of continuous feeding.

19. A process according to claim 1, wherein the reaction zone initially contains a substrate concentration of 0.5 to 40 $g \cdot l^{-1}$ of initial reaction volume, and the substrate is continuously supplied to said strain after the initial substrate concentration is 0.1 to 15 $g \cdot l^{-1}$.

20. A process according to claim 19, wherein the substrate is continuously supplied to said strain when the initial substrate concentration is between 0.1 and 5 $g \cdot h^{-1} \cdot l^{-1}$.

21. A process according to claim 1, wherein said flow rate of continuous feeding of the substrate is decreased at least once during said culturing and the culturing is continued at said decreased flow rate of continuous feeding.

22. A process according to claim 21, wherein said flow rate is decreased at least twice and the culturing is continued at said decreased flow rates of continuous feeding.

23. In a process for the fed batch production of a composition of sophorosides, comprising culturing a strain of *Candida bombicola* CBS 6009 in a culture medium containing a nitrogen source and a substrate under aerated culturing conditions in a reaction zone, the improvement comprising:

(a) continuously feeding said substrate to the strain in the reaction zone at a flow rate of between 0.01 and 4 grams of substrate per hour and per liter of initial reaction volume, and maintaining the residual concentration of said substrate in the reaction zone at a concentration not exceeding 18 grams per liter of initial reaction volume while said substrate is being continuously fed to the reaction zone, and (b) recovering the resultant composition of sophorosides, wherein said substrate is at least one of an animal oil, a vegetable oil, or an ester of said animal or vegetable oil, said animal or vegetable oil or said ester comprising an aliphatic, straight chain with 10 to 24 carbon atoms.

\* \* \* \* \*